(12) United States Patent
Castillo

(10) Patent No.: US 6,464,657 B1
(45) Date of Patent: Oct. 15, 2002

(54) ANATOMICAL JOINT BRACE FIELD OF THE INVENTION

(76) Inventor: James D. Castillo, P.O. Box 311, Los Alamos, CA (US) 93440

( * ) Notice: Subject to any disclaimer, the term of this patent is extended or adjusted under 35 U.S.C. 154(b) by 0 days.

(21) Appl. No.: 09/578,125

(22) Filed: May 24, 2000

(51) Int. Cl.$^7$ .................................................. A61F 5/00
(52) U.S. Cl. ................................ 602/26; 602/16; 602/5
(58) Field of Search .................................. 602/5, 16, 20, 602/23, 26; 178/878–881; 623/39

(56) References Cited

U.S. PATENT DOCUMENTS

| | | | |
|---|---|---|---|
| 1,390,915 A | | 9/1921 | Loth |
| 2,531,486 A | | 11/1950 | Weber |
| 2,883,982 A | | 4/1959 | Rainey |
| 3,030,634 A | | 4/1962 | Bair |
| 3,055,359 A | * | 9/1962 | Palmer ........................ 128/80 |
| 3,099,448 A | | 7/1963 | Salvo |
| 3,387,305 A | | 6/1968 | Shafer |
| 3,669,105 A | | 6/1972 | Castiglia |
| 3,779,654 A | | 12/1973 | Horne |
| 3,785,372 A | | 1/1974 | Craig |
| 3,817,244 A | | 6/1974 | Taylor |
| 3,900,898 A | | 8/1975 | Ackerman |
| 3,901,223 A | * | 8/1975 | May ........................ 128/80 F |

(List continued on next page.)

FOREIGN PATENT DOCUMENTS

| | | |
|---|---|---|
| DE | 1491569 | 7/1969 |
| DE | 2432766 | 3/1975 |
| EP | 297766 | 4/1989 |
| WO | 8404240 | 11/1984 |

OTHER PUBLICATIONS

"Strength and Motor Task Performance as Effected by the Carbon Titanium Knee Brace in Normal Health Males", by T.K. Iglehart, 1985, Colorado State Univ. Dept. of Physical Education, Fort Collins, Colo. Springs, 1985, pp. 1–12.

Primary Examiner—Denise Pothier
(74) Attorney, Agent, or Firm—Stetina Brunda

(57) ABSTRACT

An exteriorly positionable anatomical brace for stabilizing a unit pivoting joint disposed between a first limb structure and a second limb structure of a living being. The brace includes a first cuff partially encompassable about the first limb structure and a second cuff partially encompassable about the second limb structure. Each cuff is a generally U-shaped tensionable and flexibly bendable wall structure with two lateral cuff arms having respective distal ends arcuately extending toward each other. At least one tensioning elongate member is integral with each lateral cuff arm and has a threaded end extending from the respective distal end of the cuff. A stop member is disposed at each distal end of each cuff arm and accommodates the passage therethrough of the threaded end of the elongate member. A threaded bolt engaged thereon bendably draws each respective elongate member with respective integral lateral cuff arm progressively tighter against the respective adjacent limb structure site for stable engagement therewith. A pivotable brace joint member connects the first and second cuffs, and preferably can at least partially replicate normal multiplanar joint movement.

15 Claims, 3 Drawing Sheets

U.S. PATENT DOCUMENTS

| | | | |
|---|---|---|---|
| 3,902,482 | A | 9/1975 | Taylor |
| 3,928,872 | A | 12/1975 | Johnson |
| 3,958,569 | A | 5/1976 | Vosburgh |
| 4,136,404 | A | 1/1979 | Lange |
| 4,169,467 | A | 10/1979 | Robischong et al. |
| 4,241,730 | A | 12/1980 | Helfet |
| 4,271,831 | A | 6/1981 | Deibert |
| 4,361,142 | A | 11/1982 | Lewis et al. |
| 4,372,298 | A | 2/1983 | Lerman |
| 4,381,768 | A | 5/1983 | Erichsen et al. |
| D269,379 | S | 6/1983 | Bledsoe |
| 4,407,276 | A | 10/1983 | Bledsoe |
| 4,428,369 | A | 1/1984 | Peckham et al. |
| 4,487,200 | A | 12/1984 | Feanny et al. |
| 4,489,718 | A | 12/1984 | Martin |
| 4,493,316 | A | 1/1985 | Reed et al. |
| 4,494,534 | A | 1/1985 | Hutson |
| 4,503,846 | A | 3/1985 | Martin |
| 4,523,585 | A | 6/1985 | Lamb et al. |
| 4,554,913 | A | 11/1985 | Womack et al. |
| D284,702 | S | 7/1986 | Castillo |
| 4,599,998 | A | 7/1986 | Castillo |
| 4,603,690 | A | 8/1986 | Skeen |
| 4,614,181 | A | 9/1986 | Karlsson |
| 4,620,532 | A | 11/1986 | Houswerth |
| 4,621,624 | A | 11/1986 | Rayboy |
| 4,628,916 | A | 12/1986 | Lerman et al. |
| 4,665,905 | A | 5/1987 | Brown |
| 4,681,097 | A | 7/1987 | Pansiera |
| 4,697,583 | A | 10/1987 | Mason et al. |
| 4,699,129 | A | 10/1987 | Aaserude et al. |
| 4,715,363 | A | 12/1987 | Detty |
| 4,723,539 | A | 2/1988 | Townsend |
| 4,753,240 | A | 6/1988 | Sparks |
| D298,568 | S | 11/1988 | Womack et al. |
| 4,791,916 | A | 12/1988 | Paez |
| 4,803,975 | A | 2/1989 | Meyers |
| 4,854,308 | A | 8/1989 | Drillio |
| 4,856,501 | A | 8/1989 | Castillo et al. |
| 4,886,054 | A | 12/1989 | Castillo et al. |
| 4,928,676 | A * | 5/1990 | Pansiera .................. 128/80 F |
| 4,938,207 | A | 7/1990 | Vargo |
| 4,940,044 | A | 7/1990 | Castillo |
| 4,964,402 | A | 10/1990 | Grim et al. |
| 4,986,264 | A | 1/1991 | Miller |
| D318,736 | S | 7/1991 | Castillo |
| 5,063,916 | A | 11/1991 | France et al. |
| 5,121,742 | A | 6/1992 | Engen |
| 5,135,469 | A * | 8/1992 | Castillo ....................... 602/16 |
| 5,230,697 | A | 7/1993 | Castillo et al. |
| 5,288,287 | A | 2/1994 | Castillo et al. |
| D346,028 | S | 4/1994 | Lengvel |
| D357,070 | S | 4/1995 | Castillo |
| 5,547,464 | A * | 8/1996 | Luttrell et al. ................ 602/26 |
| 6,319,216 | B1 * | 11/2001 | Coligado ....................... 602/5 |

* cited by examiner

ANATOMICAL JOINT BRACE FIELD OF THE INVENTION

FIELD OF THE INVENTION

This invention relates in general to braces for human joint support, and in particular to an exteriorly positionable anatomical brace having tensionably tightenable cuffs situated about respective limb structures on either side of a uniting pivoting joint such as a knee joint to thereby provide adjustable tightening pressure on the limb structures and resulting stability to the supported joint.

BACKGROUND OF THE INVENTION

Both injury and disease can affect the health, well-being, and operability of various joints of the human body. Chief among such joints are the knee and elbow where disease such as osteo-arthritis can curtail normal activity or where an injury such as a sports-related abuse or impact can prevent or severely limit continued activity. One manner of treating such joint conditions is to fit the wearer with an appropriate brace whereby a pivotal support member is positioned adjacent the affected joint and held in place usually by cuff members-situated around limb structure sites above and below the supported joint. As is apparent, the cuff members are responsible for stabilizing the support member and therefore must be well secured to their associated limbs. To accomplish such securement, present cuff members are typically provided with one or more straps that are tightened around each limb structure and retained by buckles, hook-and-loop connections, or the like. Concurrently, the support member adjacent the joint may well be pivotal in solely a single plane and thus limit the normal multi-planar mobility of the joint.

Such present-day construction is generally deficient, however, in that such cuff tightening is limited by strength of the user as well as flexibility and tensionabilitity of the cuff structure itself, while such joint construction prevents normal twistability between the pivoting limbs. In view of these deficiencies, it is apparent that a need is present for an exteriorly positionable anatomical brace wherein the tightness of cuff members can easily be adjusted for effective brace engagement.

Another object of the present invention is to provide an anatomical brace wherein cuff-member structure is adjustably tensionable in contact with adjacent encompassed limb structures to thereby effectively anchor the cuff to the limb.

Still another object of the present invention is to provide an anatomical brace wherein the pivotable brace joint member thereof connecting the first and second cuffs and supportingly adjacent the joint itself is constructed to permit limited multi-planar movement between the two cuffs that endeavors to replicate normal joint movement.

These and other objects of the present invention will become apparent throughout the description thereof which now follows.

SUMMARY OF THE INVENTION

The present invention is an exteriorly positionable anatomical brace for stabilizing a uniting pivoting joint disposed between a first limb structure and a second limb structure of a living being. The brace includes a first cuff partially encompassable about the first limb structure and a second cuff partially encompassable about the second limb structure. Each cuff is a generally U-shaped tensionable and flexibly bendable wall structure with two lateral cuff arms having respective distal ends arcuately extending toward each other for juxtapositioning with respective adjacent limb structure sites. At least one tensioning elongate member is integral with each lateral cuff arm and has a threaded end extending from the respective distal end of the cuff. A stop member is disposed at each distal end of each cuff arm and accommodates the passage therethrough of the threaded end of the respective at least one tensioning elongate member. A threaded bolt is engaged on the threaded end of the respective at least one tensioning elongate member and is rotatably movable thereon against the stop member for bendably drawing each respective elongate member with the respective integral lateral cuff arm progressively tighter against the respective adjacent limb structure site in direct relationship to the magnitude of rotational movement of the bolt against the stop member. Finally, a pivotable brace joint member connects the first and second cuffs through respective first and second rigid frame members extending from each respective first and second cuff.

Preferable brace joint construction includes a forward arm member having a generally spherical first end and a generally spherical second end, and a rearward arm member in tandem relationship with the forward arm member and likewise having a generally spherical first end and a generally spherical second end. The joint has a first end attached to the first frame member and a second end attached to the second frame member, with each end having two generally spherical sockets positioned such that each spherical socket accommodates one respective spherical end of each respective arm member for limited multiplanar movement between the rigid frame members and therefore between the first and second cuff.

Employment of the anatomical brace here defined provides adjustably tightenable cuff engagement with encompassed limb structure sites by rotating the respective bolt threaded on each elongate member and drawing the cuff to the limb structure site to thereby maximize stability of the brace with the limb. Simultaneously, because of the spherically cooperative configurations of the brace joint and the resulting multiplanar movement potential between the two cuffs of the brace, the supported joint can simultaneously experience a more normal replication of natural movement.

BRIEF DESCRIPTION OF THE DRAWINGS

An illustrative and presently preferred embodiment of the invention is shown in the accompanying drawings in which:

FIG. 2c is a top plan, view along line 2c—2c of FIG. 2a;

DETAILED DESCRIPTION OF THE PREFERRED EMBODIMENT

Figure 1:
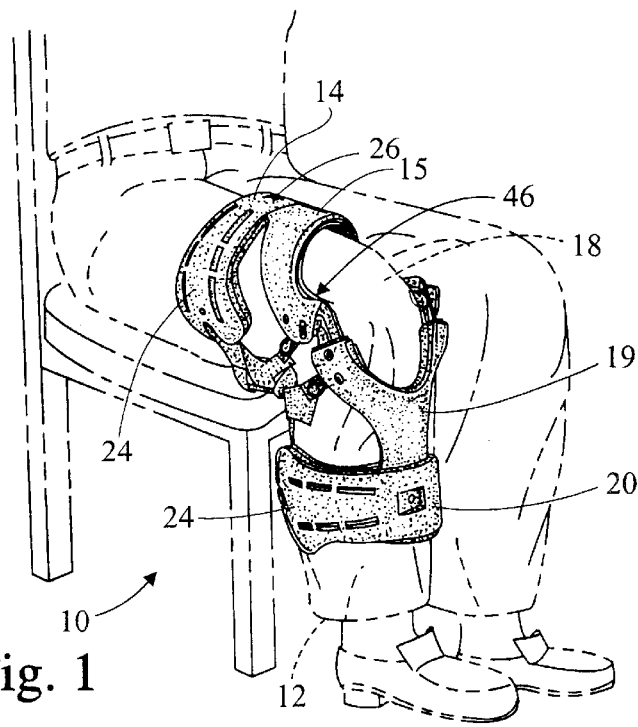
FIG. 1 is a perspective view of an exteriorly positionable knee brace with cuffs in place on a user's leg shown in phantom.
Figure 3:
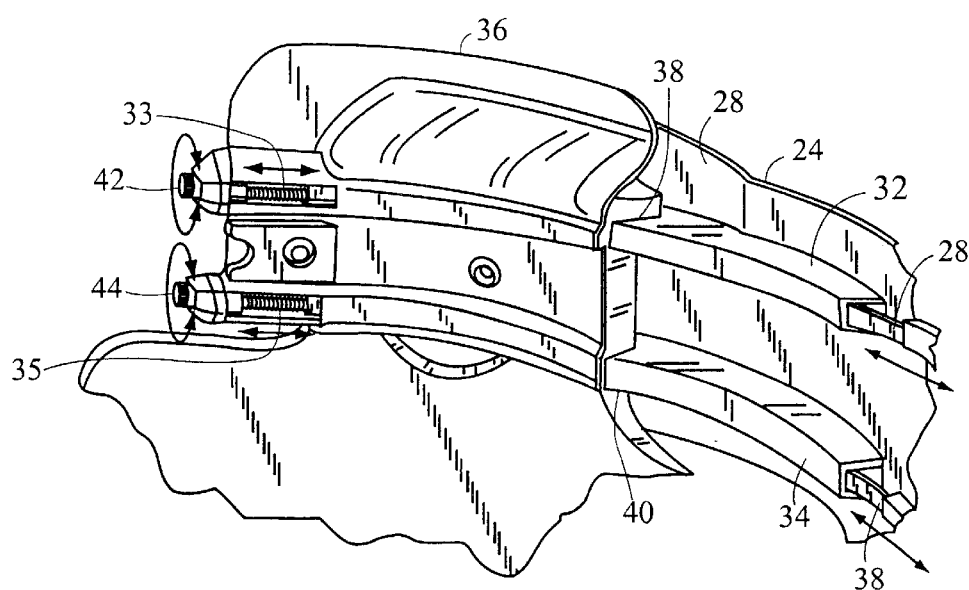
FIG. 3 is an interior perspective view of one arm of the cuff of the brace of FIG. 1 with a stop member in place.

Referring to FIGS. 1–3, an exteriorly positionable anatomical brace 10 is shown in place on a leg 12, shown in phantom, of a human being. The brace 10 has a first cuff 14 encompassed about the limb structure above the knee joint 18 and a second cuff 20 encompassed about the limb structure below the knee joint 18. Each cuff 14, 20 is a generally U-shape flexibly bendable and tensionable wall structure, which non-limitedly can be fabricated of a polymer plastic, and has two identical mirror-image lateral arms 24, 26 (the latter slightly visible in FIG. 1). Each arm 24, 26 has a distal end 27 arcuately extending inwardly toward the opposing mirror-image distal end of the respective opposing arm for juxtapositioning with adjacent sites of respective limb structures.

Figure 2A:
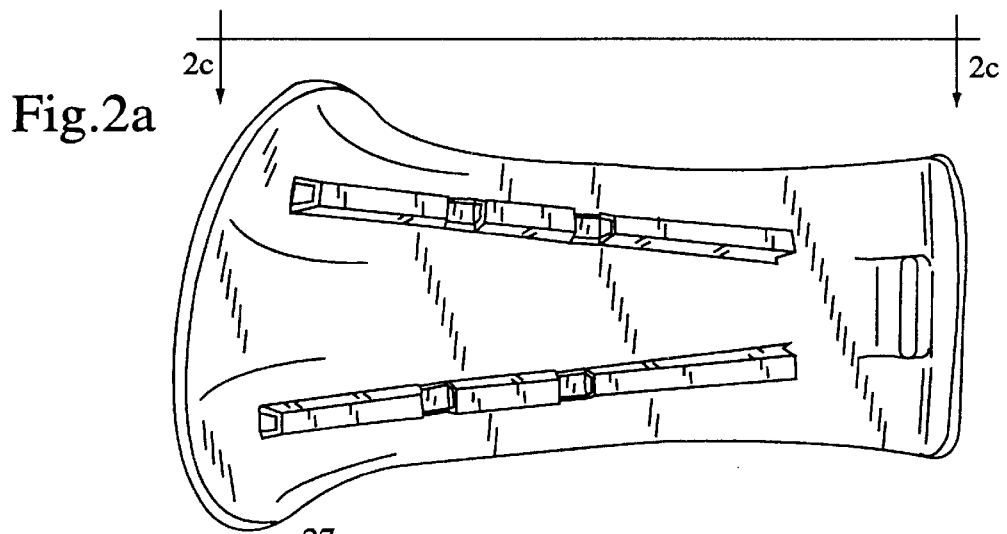
FIG. 2a is an interior side elevation view of one arm of the cuff of the brace of FIG. 1.

As shown particularly in FIGS. 2a and 3 with respect to one lateral arm 24, whose following description also applies to the second lateral arm 26, the arm 24 has two parallel tensioning elongate strips members 28, 30, here non-limitedly fabricated of titanium or a polymer composite, integral therewith and disposed within respective parallel sleeves 32, 39 that are structurally a part of the arm 24. While two strip members 28, 30 are shown, it is to be understood that a single strip member or more than two strip members, can be employed. Each strip member 28, 30 has a respective threaded end 33, 35 extending from the sleeves 32, 34 for passage through a stop member non-limitedly exemplified as a cuff extender 36. The cuff extender 36 is arcuately shaped to compliment an adjacent limb structure and has two receptor channels 38, 40 for receiving and retaining therein each respective sleeve 32, 34 as shown clearly in FIG. 3. Strip member threaded ends 33, 35 extend exteriorly of the cuff extender 36 and have threaded thereon respective bolts 42, 49 for rotational movement on the threaded strip ends 33, 35.

Figure 4:
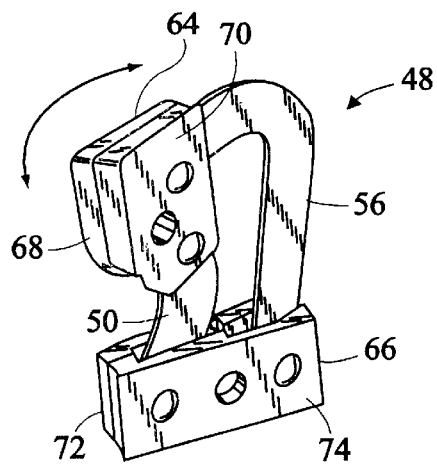
FIG. 4 is a perspective view of a pivotable brace joint for joining the cuffs of FIG. 1 to each other.
Figure 5:
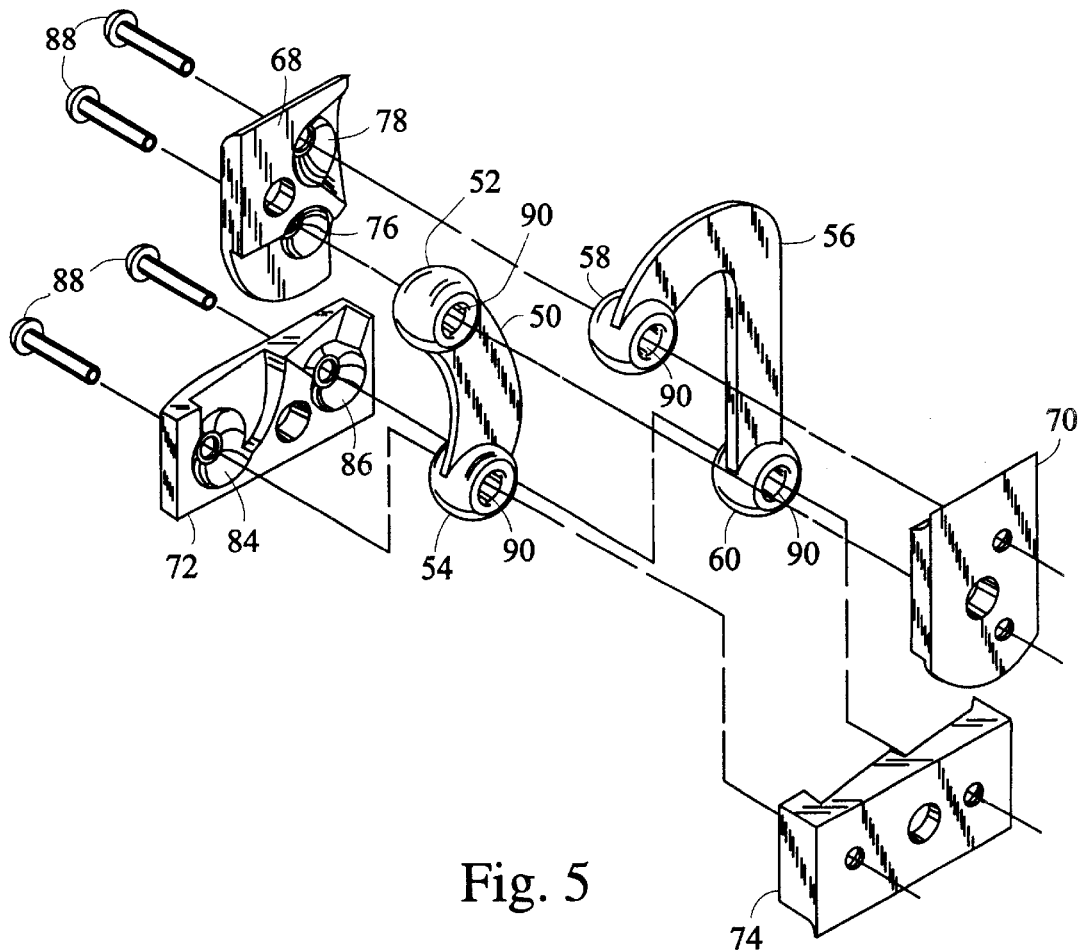
FIG. 5 is a perspective disassembled view of the joint of FIG. 4.

Referring to FIGS. 1, 4, and 5, a non-limitedly exemplified pivotal brace joint member 46 connects first and second respective rigid frame members 15, 19 extending from respective cuffs 14, 20 to each other and has two identical opposing pivoting assemblies 48 each on one lateral side of the natural uniting pivoting knee joint 18 which, of course, unites the two limb structures. The pivoting assembly 48 includes a forward arm member 50 having a generally spherical first end 52 and a generally spherical second end 54, and a rearward arm member 56 in tandem relationship with the forward arm member 50 and having a generally spherical first end 58 and a generally spherical second end 60. The pivoting assembly 48 additionally includes a first end 64 attached to the first frame member 15 and a second end 66 attached to the second frame member 19. The joint structure has four mating pieces 68, 70, 72, 74 that accept the forward and rearward arm members 50, 56. In particular, mating pieces 68 and 70 each have mating spherical sockets 76, 78 that accept, respectively, spherical ends 52 and 58 of forward and rearward arm members 50, 56. Mating pieces 72, 74 each having mating spherical sockets 84, 86 that accept, respectively, spherical ends 54 and 60 of forward and rearward arm members 50, 56. Conventional securement pins 88 maintain the forward and rearward arm members 50, 56 between the respective mating pieces 68, 70 and 72, 74. While the pins 88 pass through apertures 90 of the spherical ends 52, 54, 58, 60, the diameter of the pins 88 is less than the diameter of the apertures 90 to thereby permit limited multiplanar movement of the respective spherical ends within their respective spherical sockets. Such multiplanar movement of the spherical ends results in multiplanar movement of the frame members 15, 19 relative each other to thereby at least parts ally replicate natural dissimilar pivotal movement of inner and outer joint interactions that normally occurs in a health joint.

Figure 2B:
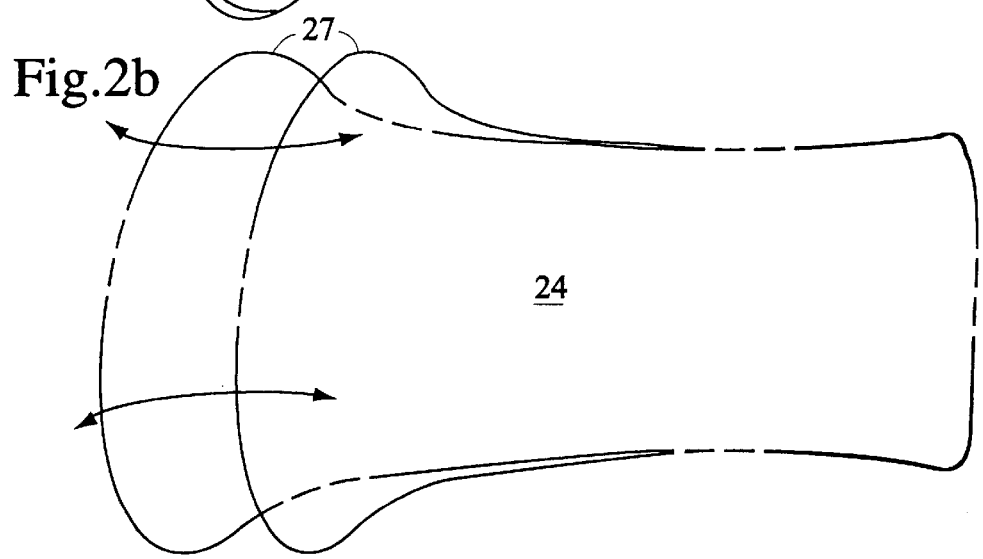
FIG. 2b is a schematic interior side elevation view of the arm of FIG. 2a showing tensioning thereof.
Figure 2C:
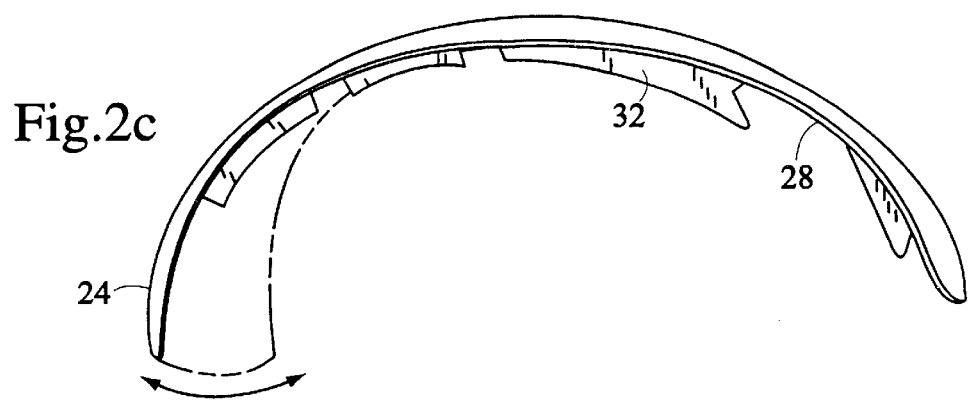

In operation, the brace 10 is fitted to a user by encompassing the first cuff 14 about the first limb structure above the knee joint 18 and the second cuff 20 about the second limb structure below the knee joint 18 as generally shown in FIG. 1 such that the knee joint 18 has juxtaposed therewith the brace joint member 46. It is, of course, to be understood that while a knee joint is here illustrated, a brace constructed according to the present invention can be provided for other anatomical joints as would be recognized by a skilled artisan. Preferably, a standard buckle-type strap or similar connector can be included with each cuff 14, 20 to extend between the opposing distal ends 28 thereof for non-slip positioning of the cuffs 14, 20 prior to tightening. Once the cuffs 14, 20 are situated about the limb structures, the bolts 42, 44 are rotated on the threaded ends 33, 35 of the strip members 28, 30 to thereby cause movement of the distal ends 27, as illustrated in FIGS. 2b and 2c, against the limb structures as the strip members 28, 30 and lateral arms 24, 26 are forced to bend toward the encompassed limb structures. Continued bolt rotation increases tightening of the lateral arms 24, 26 against the encompassed limb structures to thereby accomplish superior anchoring of the brace 10 as well as angular anatomy contours and consequent stabilization of the joint being supported. As earlier described, because the brace joint member 46 connecting the frame members 15, 19 of the cuffs 14, 20 preferably is constructed to include limited multiplanar movement for replication of normal joint movement, such multiplanar movement between the well-anchored cuffs 14, 20 can result in a more natural interaction between the encompassed limb structures. In this manner, a user wearing the anatomical brace here defined experiences exceptional stabilization of joint activity, yet finds fully comfortable anatomical attachment of the brace.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An exteriorly positionable anatomical brace for stabilizing a uniting pivoting joint disposed between a first limb structure and a second limb structure of a living being, the brace comprising:

a) a first cuff partially encompassable about the first limb structure and a second cuff partially encompassable about the second limb structure, wherein each said cuff is a generally U-shape flexibly bendable and tensionable wall structure with two lateral cuff arms having respective distal ends arcuately extending toward each other for juxtapositioning with respective adjacent limb structure sites with said respective first and second cuffs having extending therefrom respective first and second rigid frame members, each of the lateral cuff arms further having at least one sleeve;

b) at least one tensioning elongate member integral with each lateral cuff arm and having a threaded end extending from the respective distal end of each cuff arm, at least a portion of each of the at least one tensioning elongate member being retained within the respective at least one sleeve;

c) a stop member disposed at each distal end of each cuff arm, said stop member accommodating the passage therethrough of the threaded end of the respective at least one tensioning elongate member;

d) a threaded bolt engaged on the threaded end of the respective at least one tensioning elongate member and rotatably movable thereon against the stop member for bendably drawing each respective elongate member with respective integral lateral cuff arm progressively tighter against the respective adjacent limb structure site in direct relationship to the magnitude of rotational movement of said bolt against the stop member; and e) a pivotable brace joint member connecting the first and second rigid frame members.

2. An exteriorly positionable anatomical brace as claimed in claim 1 wherein the at least one tensioning elongate member is fabricated of a polymer composite.

3. An exteriorly positionable anatomical brace as claimed in claim 2 wherein the at least one tensioning elongate member is titanium.

4. An exteriorly positionable anatomical brace as claimed in claim 1 wherein the stop member is a cuff extender arcuately shaped for juxtaposition with the respective limb structure and having a respective receptor channel for retaining therein each respective at least one sleeve of each lateral cuff arm.

5. An exteriorly positionable anatomical brace as claimed in claim 4 having two parallel tensioning elongate members integral with each lateral cuff arm.

6. An exteriorly positionable anatomical brace as claimed in claim 1 having two parallel tensioning elongate members integral with each lateral cuff arm.

7. An exteriorly positionable anatomical brace for stabilizing a uniting pivoting joint disposed between a first limb structure and a second limb structure of a living being, the brace comprising:

a) a first cuff partially encompassable about the first limb structure and a second cuff partially encompassable about the second limb structure, wherein each said cuff is a generally U-shape flexibly bendable and tensionable wall structure with two lateral cuff arms having respective distal ends arcuately extending toward each other for juxtapositioning with respective adjacent limb structure sites with said respective first and second cuffs having extending therefrom respective first and second rigid frame members;

b) at least one tensioning elongate member integral with each lateral cuff arm and having a threaded end extending from the respective distal end of each cuff arm;

c) a stop member disposed at each distal end of each cuff arm, said stop member accommodating the passage therethrough of the threaded end of the respective at least one tensioning elongate member;

d) a threaded bolt engaged on the threaded end of the respective at least one tensioning elongate member and rotatably movable thereon against the stop member for bendably drawing each respective elongate member with respective integral lateral cuff arm progressively tighter against the respective adjacent limb structure site in direct relationship to the magnitude of rotational movement of said bolt against the stop member; and e) a pivotable brace joint member connecting the first and second rigid frame members, said brace joint member comprising two opposing assemblies each sized and configured to be on one lateral side of the uniting pivoting joint, with each said assembly comprising:

i) a forward arm member having a generally spherical first end and a generally spherical second end, and a rearward arm member in tandem relationship with the forward arm member and having a generally spherical first end and a generally spherical second end; and ii) a first end attached to the first frame member and a second end attached to the second frame member, with each end having two generally spherical sockets positioned such that each spherical socket accommodates one respective spherical end of each respective arm member for multiplanar movement between said first and second frame members.

8. An exteriorly positionable anatomical brace as claimed in claim 7 wherein the at least one tensioning elongate member is fabricated of a metal or a polymer composite.

9. An exteriorly positionable anatomical brace as claimed in claim 8 wherein the at least one tensioning elongate member is titanium.

10. An exteriorly positionable anatomical brace as claimed in claim 7 wherein each cuff lateral arm has a respective at least one sleeve wherein at least a portion of each respective at least one tensioning elongate member is retained.

11. An exteriorly positionable anatomical brace as claimed in claim 11 wherein the stop member is a cuff extender arcuately shaped for juxtaposition with the respective limb structure and having a respective receptor channel for retaining therein each respective at least one sleeve of each lateral cuff arm.

12. An exteriorly positionable anatomical brace as claimed in claim 11 having two parallel tensioning elongate members integral with each lateral cuff arm.

13. An exteriorly positionable anatomical brace as claimed in claim 7 having two parallel tensioning elongate members integral with each lateral cuff arm.

14. An exteriorly positionable anatomical brace for stabilizing a uniting pivoting joint disposed between a first limb structure and a second limb structure of a living being, the brace comprising:

a first cuff partially encompassable about the first limb structure and a second cuff partially encompassable about the second limb structure, each of said cuffs including two lateral cuff arms having respective distal ends arcuately extending toward each other for juxtapositioning with respective adjacent limb structure sites, each of said lateral cuff arms further having at least one sleeve;

at least one tensioning elongate member integral with each lateral cuff arm and having a threaded end extending from the respective distal end of each cuff arm, wherein at least a portion of each of the at least one tensioning elongate member is retained within the respective at least one sleeve;

a stop member disposed at each distal end of each cuff arm, said stop member accommodating the passage therethrough of the threaded end of the respective at least one tensioning elongate member; and a threaded bolt engaged on the threaded end of the respective at least one tensioning elongate member and rotatably movable thereon against the stop member for bendably drawing each respective elongate member with respective integral lateral cuff arm progressively tighter against the respective adjacent limb structure site in direct relationship to the magnitude of rotational movement of said bolt against the stop member.

15. An exteriorly positionable anatomical brace for stabilizing a uniting pivoting joint disposed between a first limb structure and a second limb structure of a living being, the brace comprising:

a first cuff partially encompassable about the first limb structure and a second cuff partially encompassable about the second limb structure, each of said cuffs including two lateral cuff arms having respective distal ends arcuately extending toward each other for juxtapositioning with respective adjacent limb structure sites with said first cuff extending therefrom a first rigid frame member and said second cuff extending therefrom a second rigid frame member; and a pivotable brace joint member connecting the first and second rigid frame members, said brace joint member comprising two opposing assemblies each sized and configured to be on one lateral side of the uniting pivoting joint, with each said assembly comprising:

i) a forward arm member having a generally spherical first end and a generally spherical second end, and a rearward arm member in tandem relationship with the forward arm member and having a generally spherical first end and a generally spherical second end; and ii) a first end attached to the first frame member and a second end attached to the second frame member, with each end having two generally spherical sockets positioned such that each spherical socket accommodates one respective spherical end of each respective arm member for multiplanar movement between said first and second frame members.

* * * * *

UNITED STATES PATENT AND TRADEMARK OFFICE
CERTIFICATE OF CORRECTION

PATENT NO. : 6,464,657 B1
DATED : October 15, 2002
INVENTOR(S) : James D. Castillo It is certified that error appears in the above-identified patent and that said Letters Patent is hereby corrected as shown below:

<u>Title page,</u>
Item [54], Title, please delete "FIELD OF THE INVENTION".

Signed and Sealed this

Twenty-third Day of September, 2003

JAMES E. ROGAN
*Director of the United States Patent and Trademark Office*